United States Patent [19]

Schrank et al.

[11] 4,411,894
[45] Oct. 25, 1983

[54] PHARMACEUTICAL PREPARATIONS

[75] Inventors: Jürg Schrank, Riehen; Hans Steffen, Arisdorf, both of Switzerland

[73] Assignee: Hoffmann-La Roche Inc., Nutley, N.J.

[21] Appl. No.: 293,587

[22] Filed: Aug. 17, 1981

Related U.S. Application Data

[63] Continuation of Ser. No. 159,441, Jun. 13, 1980, abandoned.

[30] Foreign Application Priority Data

Jun. 22, 1979 [CH] Switzerland .......................... 5863/79

[51] Int. Cl.³ .................... A61K 31/33; A61K 31/685
[52] U.S. Cl. ................................... 424/199; 424/244; 424/258
[58] Field of Search ............................... 424/199, 244

[56] References Cited

U.S. PATENT DOCUMENTS 4,158,707  6/1979  Steffen ................................ 424/244

FOREIGN PATENT DOCUMENTS 2656333  6/1978  Fed. Rep. of Germany .
2818655  11/1978  Fed. Rep. of Germany .
2081586  12/1971  France .
2298318  8/1976  France .
2002319  2/1979  United Kingdom .

OTHER PUBLICATIONS

Chem. Abst., 84, 41686, (1970).
Chem. Abst., 90, 35233p, (1979).
Chem. Abst., 78, 128390e, (1973).
Chem. Abst., 94, 60277w, (1981).

*Primary Examiner*—Stanley J. Friedman
*Attorney, Agent, or Firm*—Jon S. Saxe; George M. Gould; John J. Maitner

[57] ABSTRACT

Pharmaceutical compositions useful for the parenteral administration of fat-soluble medicaments are disclosed. The compositions comprise, in addition to the medicaments, a sugar-containing liposome solution or lyophilizates thereof.

8 Claims, No Drawings

PHARMACEUTICAL PREPARATIONS

This is a continuation of application Ser. No. 159,441 filed June 13, 1980, now abandoned.

BACKGROUND OF THE INVENTION

Heretofore, vehicles for the parenteral administration of many fat-soluble pharmaceutically active materials were not readily available. In addition, when such vehicles were prepared, their parenteral administration often resulted in many undesirable side-effects such as hemolysis, phlebothromboses or blood coagulation.

Parenteral administration of fat-soluble pharmaceutically active material has been achieved using liposome solutions. In these compositions, the active materials can be parenterally administered without the above undesirable side-effects and without any loss in their biological activity.

The preparation of pharmaceutically acceptable liposome solutions has been known for some time. Information about such compositions have been presented by G. Gregoriadis ("Liposomes or Drug Carriers in Biology and Medicine") and B. E. Ryman ("Liposome Delivery of Materials of Therapeutic Interest—Possibilities and Problems") in the Abstracts of the symposium entitled "The Potential of Liposomes as Drug Carriers", Battelle Institute, Geneva, Switzerland, March, 1978, pp. 5-11 and 26-31. However, difficulties were and continue to be encountered with the long term stability of such solutions. Stability of such solutions depends on both the composition of the lipid phase and the composition of the aqueous phase. In addition, the presence of even minor impurities in the solutions can lead to floculation.

It has now been found that stable liposome solutions suitable for parenteral administration can be prepared by the addition of sugars to the liposome solutions as protective colloids.

SUMMARY OF THE INVENTION

The present invention is directed to pharmaceutical compositions for the parenteral administration of fat-soluble medicaments which heretofore could either not be parenterally administered or, if so administered, would cause undesirable side-effects. These compositions comprise the fat-soluble medicament in an aqueous liposome solution having a relatively high sugar concentration or a lyophilizate thereof. This invention is also directed to processes for making such compositions and to the use of liposome components in such compositions.

DETAILED DESCRIPTION OF THE INVENTION

This invention is directed to pharmaceutical compositions for the parenteral administration of fat-soluble medicaments, i.e. pharmaceutically active ingredients, to processes for preparing such compositions and to the liposome components of these compositions.

The liposome components of these pharmaceutical compositions are lipids and, in particular, phospholipids. The preferred phospholipids are the lecithins. Lecithins are mixed esters of glycerol and choline with fatty acids and phosphoric acid having the formula

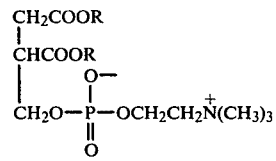

wherein R is a fatty acid radical. Lecithins can be of a vegetable, animal or synthetic origin as, for example, soya lecithin, egg lecithin or L-$\beta$-oleoyl-2-palmitoyl-$\alpha$-lecithin.

The liposomes can be synthesized either monolamellar or multilamellar and preferably have a diameter of 250-2000 Å (Angstroms). Monolamellar liposomes are preferred for intravenous administration.

The concentration of the liposome component in the solution generally lies in the range of from about 1% to about 25% (weight/volume) and preferably between about 5% and about 15% weight/volume.

An essential ingredient of the pharmaceutical compositions of this invention is a sugar which functions as a protective colloid and provides long-term stability to the compositions. The sugar component can be the usual monosaccharides and disaccharides or it can be a sugar-like polyol. Examples of suitable sugar components include glucose, fructose, saccharose, sorbitol and xylitol.

To achieve the desired stabilizing effect, the concentration of the sugar component in the liposome solution should be at least 0.4 molar. The upper limit of the sugar component concentration is not critical and is determined mainly by the viscosity.

Fat-soluble pharmaceutically active materials which heretofore could not be parenterally administered or, if so administered, would cause undesirable side-effects, include, for example, benzodiazepines and quinolinemethanol derivatives such as 7-chloro-1,3-dihydro-1-methyl-5-phenyl-2H-1,4-benzodiazepin-2-one (diazepam), 5-(o-fluorophenyl)-1,3-dihydro-1-methyl-7-nitro-2H-1,4-benzodiazepin-2-one (flunitrazepam) and erythro-$\alpha$-2-piperidyl-2,8-bis-(trifluoromethyl)-4-quinolinemethanol (mefloquin) or salts thereof with a physiologically compatible organic or inorganic acid usual for such purpose. These acids include hydrochloric acid, sulfuric acid, phosphoric acid, formic acid, acetic acid, oxalic acid, tartaric acid, maleic acid, benzoic acid, succinic acid, fumaric acid, levulinic acid, salicylic acid, citric acid, isocitric acid, adipic acid, lactic acid, $\alpha$-ketoglutaric acid, malic acid, malonic acid, glyceric acid, mevalonic acid, glucuronic acid, neuraminic acid, glutaric acid, aspartic acid, gluconic acid, mandelic acid, ascorbic acid, lactobionic acid, glucoheptonic acid, glutamic acid, nicotinic acid, pantothenic acid, folic acid, adenylic acid, geranylic acid, cytidylic acid and inosinic acid.

Other fat-soluble pharmaceutically active materials which can be utilized in the pharmaceutical compositions of this invention are the tricyclic antidepressants and neuroleptics, e.g. dibenzothiepins as disclosed in German Offenlegungsschrift No. 24 12 522.

The concentration of the medicament in these pharmaceutical compositions is mainly determined by its biological activity. Thus, diazepam can be used in a concentration of from about 0.1 mg/ml to about 10 mg/ml with about 5 mg/ml preferred. Mefloquin can be used in a concentration of from about 1 mg/ml to about 30 mg/ml with a range of from about 5 mg/ml to about 20 mg/ml preferred.

For the purposes of this invention, neither the concentration of the liposome component nor the concentration of the active component is critical.

The liposome compositions of this invention can also contain pharmaceutical adjuvants. Examples of such optional pharmaceutical adjuvants include those substances which are usual in compositions such as small amounts of other lipids, e.g., cholesterol, antioxidants, synergists, preserving agents, stabilizing agents, buffers for adjusting to the desired pH value or agents for adjusting the osmotic pressure. The requisite and optimum amounts of these pharmaceutical adjuvants can vary with the specific compositions.

The pharmaceutical compositions of this invention can be prepared by known procedures. For example the pharmaceutically active material can be homogenized in an aqueous solution with the liposome component and a sugar and, if desired, in the presence of the adjuvants. The homogenization is preferably carried out under pressure (e.g. 300 bar and above) and, if desired, by ultrasonics.

In an alternative procedure, the detergent can first be separated (e.g. by dialysis or gel chromatography) from the lecithin-detergent mixed micelles containing the pharmaceutically active material and a sugar can be then added to the composition. Cholanic acids are detergents which are especially preferred for this procedure with gel chromatography carried out, for example, on Sephadex 50. For dialysis, a Union Carbide dialysis tube can be used.

The resulting liposome solution can be sterilized and, if desired, lyophilized.

Solutions suitable for injection or infusion can be reconstituted from the lyophilizates shortly before use in the usual manner, e.g. by adding water or isotonic salt solution.

The following Examples illustrate this invention.

EXAMPLE 1

1000 mg of mefloquin hydrochloride and 5 g of purified soya lecithin were dissolved with 0.7 M saccharose solution in 0.067 M phosphate buffer (pH 7) ($Na_2HPO_4/NaH_2PO_4$) to a total volume of 50 ml. The solution was homogenized using a Polytron homogenizer until it was uniformly milky and individual particles were no longer visible to the naked eye. The homogenized solution was ultrasonically irradiated under a nitrogen atmosphere and at a temperature below 25° C. using a Branson ultrasonic finger at about 70 W for about 60 minutes. The resulting liposomes were separated by centrifuging for 15 minutes in a centrifuge (6000×g). The solution was filtered sterile at 120° C. for 20 minutes, sterilized and subsequently lyophilized. An injection solution was reconstituted from the lyophilizate by adding water. The diameter of the particles in the injection solution were the same as in the solution prior to the lyophilization.

EXAMPLE 2

25 g of purified soya lecithin, 62.5 g of saccharose, 825 mg of diazepam and 185 ml of 1.15 M phosphate buffer (pH 7), under a nitrogen atmosphere, were homogenized using a Polytron homogenizer until the mixture was uniformly milky. The mixture was further homogenized in circulation under a pressure of 500 atmospheres at 20° C. (The mixture flowed through the homogenizer about 60 times.) An opalescent diazepam-liposome solution resulted. This solution was filtered sterile and sterilized.

EXAMPLE 3

5 g of purified soya lecithin and 50 mg of flunitrazepam were dissolved in 20 ml of ethanol. The ethanol was then removed on a rotary evaporator. Thereafter, 6.37 g of sorbitol and 50 mg of sodium pyrosulfite antioxidant were added. The mixture was made up with 1.15 M phosphate buffer to 50 ml.

EXAMPLE 4

5 g of purified soya lecithin and 50 mg of flunitrazepan were dissolved in 20 ml of ethanol. The ethanol was then removed on a rotary evaporator. Thereafter, 16 g of glucose and 50 mg of sodium pyrosulfite antioxidant were added. The mixture was made up with 1/15 M phosphate buffer to 50 ml.

What is claimed is:

1. A pharmaceutical composition suitable for parenteral administration of fat-soluble pharmaceutically-active materials which comprises pharmaceutical adjuvants, a fat-soluble pharmaceutically-active material selected from the group consisting of a benzodiazepine or quinolinemethanol derivative, a lecithin of vegetable or animal origin and a sugar component selected from the group consisting of monosaccharides and disaccharides.

2. A pharmaceutical composition suitable for parenteral administration of fat soluble pharmaceutically-active materials which comprises pharmaceutical adjuvants, a fat-soluble pharmaceutically-active material selected from the group consisting of diazepam, 7-chloro-1,3-dihydro-1-methyl-5-phenyl-2H-1,4-benzodiazepin-2-one; flunitrazepam, 5-(o-fluorophenyl)-1,3-dihyrdo-1-methyl-7-nitro-2H-1,4-benzodiazepin-2-one, and mefloquin, erythro-α-2-piperidyl-2,8 bis-(trifluoromethyl)-4-quinolinemethanol, soya lecithin and a sugar component selected from the group consisting of a monosaccharide and disaccharide, wherein the lecithin concentration ranges, in percent by weight per volume, from about 1 percent to about 25 percent and the sugar component concentration is at least 0.4 molar.

3. The pharmaceutical composition of claim 2 wherein the composition is an aqueous lecithin solution.

4. The pharmaceutical composition of claim 2 wherein the composition is a lyophilizate of an aqueous lecithin solution.

5. The pharmaceutical composition of claim 2 wherein the lecithin ranges from about 5 percent to about 15 percent.

6. The pharmaceutical composition of claim 2 wherein the pharmaceutically-active material is a benzodiazepine.

7. The pharmaceutical composition of claim 6 wherein the benzodiazepine is 7-chloro-1,3-dihydro-1-methyl-5-phenyl-2H-1,4-benzodiazepin-2-one.

8. The pharmaceutical composition of claim 2 wherein the pharmaceutically active material is mefloquin erythro-α-2-piperidyl-2,8-bis-(trifluoromethyl)-4-quinolinemethanol.

* * * * *